(12) United States Patent
Folan

(10) Patent No.: US 11,678,970 B2
(45) Date of Patent: Jun. 20, 2023

(54) DEVICE FOR ANASTOMOTIC BYPASS

(71) Applicant: BOSTON SCIENTIFIC SCIMED, INC., Maple Grove, MN (US)

(72) Inventor: Martyn G. Folan, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 575 days.

(21) Appl. No.: 16/701,545

(22) Filed: Dec. 3, 2019

(65) Prior Publication Data
US 2020/0170776 A1 Jun. 4, 2020

Related U.S. Application Data

(60) Provisional application No. 62/774,956, filed on Dec. 4, 2018.

(51) Int. Cl.
| | |
|---|---|
| *A61F 2/06* | (2013.01) |
| *A61B 17/11* | (2006.01) |
| *A61F 2/93* | (2013.01) |
| *A61M 27/00* | (2006.01) |

(52) U.S. Cl.
CPC .............. *A61F 2/064* (2013.01); *A61B 17/11* (2013.01); *A61F 2/93* (2013.01); *A61M 27/002* (2013.01); *A61B 2017/1107* (2013.01); *A61F 2230/0095* (2013.01); *A61M 2210/1042* (2013.01); *A61M 2210/12* (2013.01)

(58) Field of Classification Search
CPC ... A61B 17/11; A61B 2017/1103; A61F 2/06; A61F 2/86; A61F 2/88; A61F 2/885; A61F 2/89; A61F 2/90; A61F 2/91; A61F 2/848; A61F 2002/8486
See application file for complete search history.

(56) References Cited

U.S. PATENT DOCUMENTS

| | | | |
|---|---|---|---|
| 5,575,818 A | 11/1996 | Pinchuk | |
| 5,741,333 A | 4/1998 | Frid | |
| 5,846,261 A | 12/1998 | Kotula et al. | |
| 6,264,689 B1 | 7/2001 | Colgan et al. | |

(Continued)

FOREIGN PATENT DOCUMENTS

| | | |
|---|---|---|
| EP | 0808138 B1 | 5/2005 |
| EP | 2322122 A1 | 5/2011 |

(Continued)

OTHER PUBLICATIONS

International Search Report and Written Opinion dated Feb. 19, 2020 for International Application No. PCT/US2019/064166.

*Primary Examiner* — Susan S Su
*Assistant Examiner* — Ted Yang
(74) *Attorney, Agent, or Firm* — Seager, Tufte & Wickhem, LLP

(57) ABSTRACT

A stent including a tubular body formed of one or more interwoven wires, a first anchor member disposed adjacent the first open end of the stent, a second anchor member disposed adjacent the second open end of the stent, and at least one divider disposed between the first and second anchor members. The first and second anchor members and the divider extend radially outward from the tubular body to divide the tubular body into at least a first saddle region extending between the first anchor member and the divider and a second saddle region extending between the second anchor member and the divider.

18 Claims, 9 Drawing Sheets

(56) References Cited

U.S. PATENT DOCUMENTS

| | | |
|---|---|---|
| 6,468,303 B1 | 10/2002 | Amplatz et al. |
| 6,616,675 B1 | 9/2003 | Evard et al. |
| 6,620,122 B2 | 9/2003 | Stinson et al. |
| 6,626,936 B2 | 9/2003 | Stinson |
| 6,663,663 B2 | 12/2003 | Kim et al. |
| 6,746,489 B2 * | 6/2004 | Dua .................... A61F 2/04 623/23.68 |
| 7,018,401 B1 | 3/2006 | Hyodoh et al. |
| 7,101,392 B2 | 9/2006 | Heath |
| 7,115,136 B2 | 10/2006 | Park et al. |
| 7,311,031 B2 | 12/2007 | McCullagh et al. |
| 7,462,192 B2 | 12/2008 | Norton et al. |
| 7,591,845 B2 | 9/2009 | Rhim et al. |
| 7,670,367 B1 | 3/2010 | Chouinard et al. |
| 7,763,011 B2 | 7/2010 | Ortiz et al. |
| 8,114,147 B2 | 2/2012 | Wood et al. |
| 8,151,682 B2 | 4/2012 | Lilburn et al. |
| 8,357,193 B2 | 1/2013 | Phan et al. |
| 8,425,539 B2 | 4/2013 | Binmoeller et al. |
| 8,454,632 B2 | 6/2013 | Binmoeller et al. |
| 8,491,649 B2 * | 7/2013 | Mach .................... A61F 2/07 138/121 |
| 8,677,874 B2 | 3/2014 | Lilburn et al. |
| 8,690,817 B2 * | 4/2014 | Assaf .................. A61B 17/1114 623/23.65 |
| 8,715,317 B1 * | 5/2014 | Janardhan ........ A61B 17/12109 606/200 |
| 9,314,324 B2 * | 4/2016 | Janardhan .............. A61B 90/39 |
| 9,993,251 B2 * | 6/2018 | Todd .................... A61B 17/1114 |
| 10,052,106 B2 * | 8/2018 | Binmoeller ......... A61B 17/1114 |
| 10,076,330 B2 | 9/2018 | Sander et al. |
| 2007/0123922 A1 | 5/2007 | Cooper et al. |
| 2009/0082803 A1 | 3/2009 | Adams et al. |
| 2011/0125249 A1 | 5/2011 | Jensen et al. |
| 2013/0012969 A1 | 1/2013 | Shin |
| 2018/0078745 A1 | 3/2018 | Gray et al. |
| 2018/0125633 A1 | 5/2018 | Fikfak et al. |
| 2018/0243114 A1 | 8/2018 | Nath |
| 2018/0280166 A1 | 10/2018 | Walsh et al. |

FOREIGN PATENT DOCUMENTS

| | | |
|---|---|---|
| EP | 0957773 B1 | 8/2011 |
| EP | 2543323 A1 | 9/2013 |
| EP | 1558149 B1 | 12/2013 |
| EP | 2754415 B1 | 5/2015 |
| EP | 2177181 B1 | 6/2015 |
| WO | 9601599 A1 | 1/1996 |
| WO | 2005011533 A1 | 10/2005 |
| WO | 2009046126 A1 | 4/2009 |
| WO | 2009140195 A1 | 11/2009 |
| WO | 2013086868 A1 | 6/2013 |
| WO | 2015195893 A1 | 12/2015 |

* cited by examiner

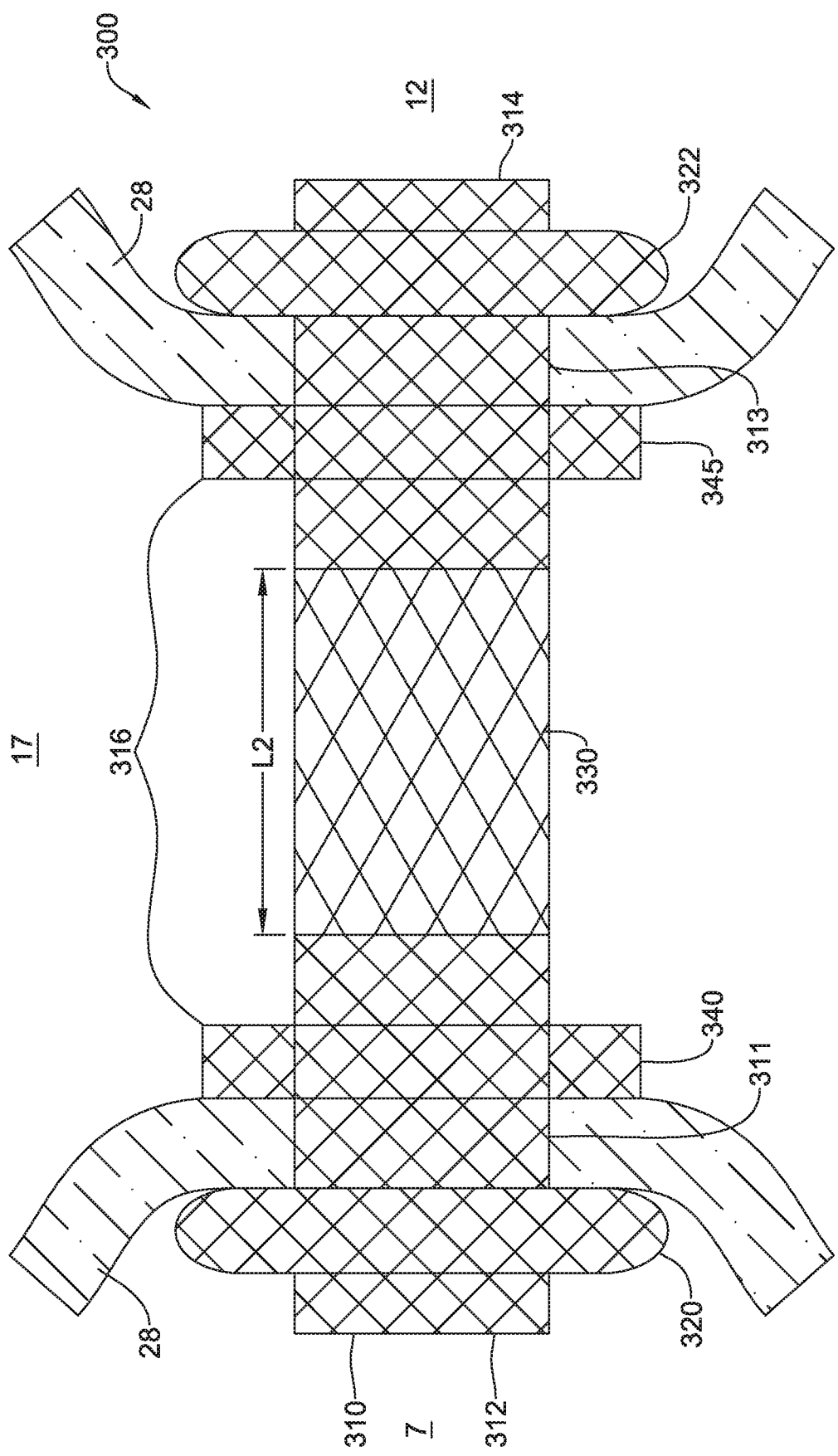

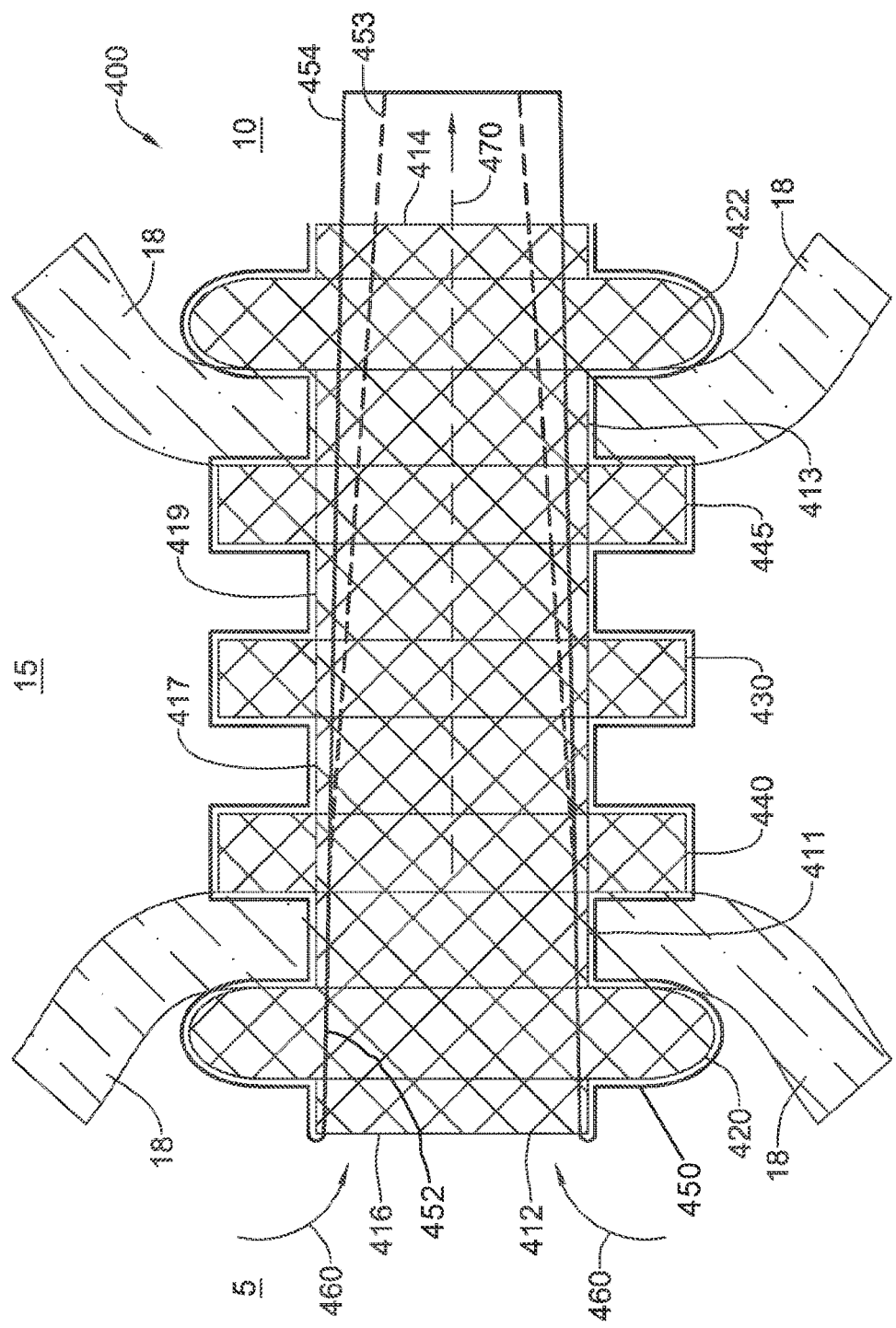

DEVICE FOR ANASTOMOTIC BYPASS

CROSS-REFERENCE TO RELATED APPLICATIONS

This application claims the benefit of priority under 35 U.S.C. § 119 of U.S. Provisional Application No. 62/774,956 filed Dec. 4, 2018, the entire disclosure of which is hereby incorporated by reference.

TECHNICAL FIELD

The present invention relates to devices, methods and systems for implanting stents. More particularly, the present invention relates to implantable stents for anastomotic bypass.

BACKGROUND

An intraluminal prosthesis is a medical device used in the treatment of bodily lumens. One type of intraluminal prosthesis used in the repair and/or treatment of diseases in various body vessels is a stent. A stent is a generally longitudinal tubular device formed of biocompatible material which is useful to open and support various lumens in the body and/or form a conduit between body lumens. For example, stents may be used in the vascular system, urogenital tract, gastrointestinal tract, esophageal tract, tracheal/bronchial tubes and bile duct, as well as in a variety of other applications in the body.

Lumen apposing metal stents (LAMS) are used to drain pseudocysts, pancreatic fluid collections and to provide direct biliary and gallbladder drainage. LAMS may be used in other locations where a conduit crossing the walls between two duct structures is desired. Accordingly, there is an ongoing need to provide alternative stent structures that provide such conduits.

SUMMARY

This disclosure provides design, material, manufacturing method, and use alternatives for medical devices.

An example medical device includes a stent comprising a tubular body formed of one or more interwoven wires, the tubular body having first and second opposing open ends and a lumen extending therebetween, the tubular body defining a longitudinal axis and a length extending between the first and second open ends, a first anchor member disposed adjacent the first open end and a second anchor member disposed adjacent the second open end, the first and second anchor members each extending radially outward from the tubular body, the first and second anchor members each having an outer diameter larger than an outer diameter of the tubular body disposed between the first and second anchor members, and at least one divider disposed between the first and second anchor members, the at least one divider extending radially outward from the tubular body and having an outer diameter larger than the outer diameter of the tubular body, the at least one divider dividing the tubular body into at least a first saddle region extending between the first anchor member and the at least one divider and a second saddle region extending between the second anchor member and the at least one divider.

Alternatively, or additionally to the example above, the first and second anchor members are interwoven with the tubular body.

Alternatively, or additionally to the example above, the first and second anchor members are less flexible than the tubular body.

Alternatively, or additionally to the example above, the at least one divider has an outer diameter larger than outer diameters of the first and second anchor members.

Alternatively, or additionally to the example above, the at least one divider includes a central divider and first and second side dividers disposed on either side of the central divider.

Alternatively, or additionally to the example above, the central divider has an outer diameter greater than outer diameters of the first and second side dividers.

Alternatively, or additionally to the example above, the central divider is more flexible than the first and second side dividers.

Alternatively, or additionally to the example above, the central divider is moveable between a first, contracted configuration in which the central divider has a first axial length, and a second, expanded configuration in which the central divider has a second axial length greater than the first axial length, the central divider expanding axially while compressing radially as it moves from the first configuration to the second configuration, wherein the length of the tubular body increases as the central divider moves between the first and second configurations.

Alternatively, or additionally to the example above, the outer diameter of the tubular body remains constant as the central divider moves between the first and second configurations.

Alternatively, or additionally to the example above, the central divider is configured to remain in the first configuration when manually moved into the first configuration, and to remain in the second configuration when manually moved into the second configuration. Alternatively, or additionally to the example above, the stent further comprises a covering extending over an entirety of an outer surface of the tubular body, first and second anchor members, and the at least one divider.

Alternatively, or additionally to the example above, the covering extends longitudinally beyond the first end of the tubular body, forming a collapsible tubular sleeve, wherein the collapsible tubular sleeve is configured to be inverted and to extend through the lumen of the tubular body from the first end of the tubular body to a free end of the collapsible tubular sleeve extending beyond the second end of the tubular body.

Alternatively, or additionally to the example above, the collapsible tubular sleeve defines a one-way valve, only allowing fluid to pass from the first end of the tubular body, through the collapsible tubular sleeve, and out the free end of the collapsible tubular sleeve.

Alternatively, or additionally to the example above, the first and second anchor members and the at least one divider extend perpendicular to the longitudinal axis.

Another example stent comprises a tubular body formed of one or more interwoven wires, the tubular body having first and second opposing open ends and a lumen extending therebetween, the tubular body defining a longitudinal axis and a length extending between the first and second open ends, and at least three longitudinally spaced apart anchor members extending radially outward from the tubular body, the anchor members each having an outer diameter larger than an outer diameter of the tubular body disposed between the anchor members, the at least three anchor members dividing the tubular body into at least a first saddle region extending between a first anchor member adjacent the first end and a center anchor member and a second saddle region extending between a second anchor member adjacent the second end and the center anchor member.

Alternatively, or additionally to the example above, the center anchor member is moveable between a first, contracted configuration in which the center anchor member has a first axial length, and a second, expanded configuration in which the center anchor member has a second axial length greater than the first axial length, the center anchor member expanding axially while compressing radially as it moves from the first configuration to the second configuration, wherein the length of the tubular body increases and the outer diameter of the tubular body remains constant as the center anchor member moves between the first and second configurations.

Alternatively, or additionally to the example above, the center anchor member is configured to remain in the first configuration when manually moved into the first configuration, and to remain in the second configuration when manually moved into the second configuration.

Alternatively, or additionally to the example above, the stent further comprises a third anchor member disposed between the first and center anchor members, and a fourth anchor member disposed between the second and center anchor members, separating the tubular body into four regions.

Alternatively, or additionally to the example above, the stent further comprises a covering extending over an entirety of an outer surface of the tubular body and the first, second, and center anchor members, wherein the covering extends longitudinally beyond the first end of the tubular body, forming a collapsible tubular sleeve, wherein the collapsible tubular sleeve is configured to be inverted and to extend through the lumen of the tubular body from the first end of the tubular body to a free end extending beyond the second end of the tubular body.

An example method of forming an anastomosis between first and second spaced apart body vessels comprises implanting a stent through a tissue wall with a first open end of the stent disposed within a first body vessel and a second open end of the stent disposed within a second body vessel, the stent including a tubular body formed of one or more interwoven wires, the tubular body defining a lumen extending between the first and second open ends, the stent including at least three longitudinally spaced apart anchor members extending radially outward from the tubular body, the anchor members each having an outer diameter larger than an outer diameter of the tubular body disposed between the anchor members, the at least three anchor members dividing the tubular body into at least a first saddle region extending between a first anchor member adjacent the first end and a center anchor member and a second saddle region extending between a second anchor member adjacent the second end and the center anchor member, wherein the stent is implanted with a first vessel wall of the first body vessel disposed within the first saddle region and a second vessel wall of the second body vessel disposed within the second saddle region, and draining fluid from the first body vessel through the lumen of the stent into the second body vessel.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

FIG. 7B is a cross-sectional view of the stent of FIG. 7A in a second configuration, disposed across vessel walls of body vessels spaced further apart=—; and FIG. 8 is a cross-sectional view of a stent in accordance with another embodiment of the disclosure.

Figure 1:
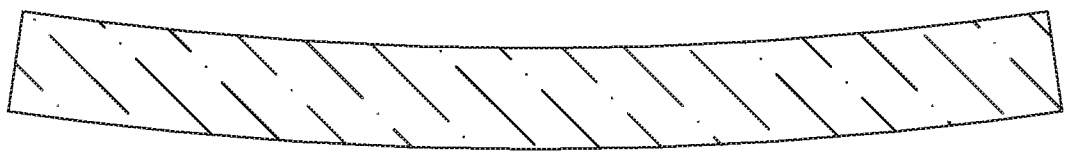
FIG. 1 is a cross-sectional view of an example body structure including first and second spaced apart body vessels.
Figure 1:
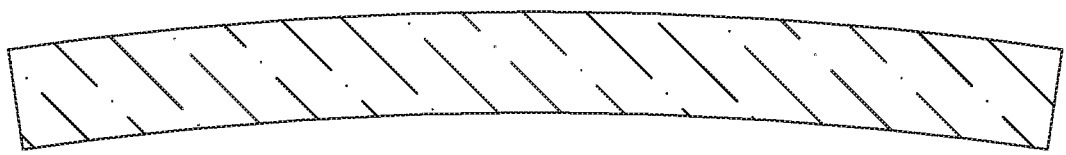

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

Figure 2:
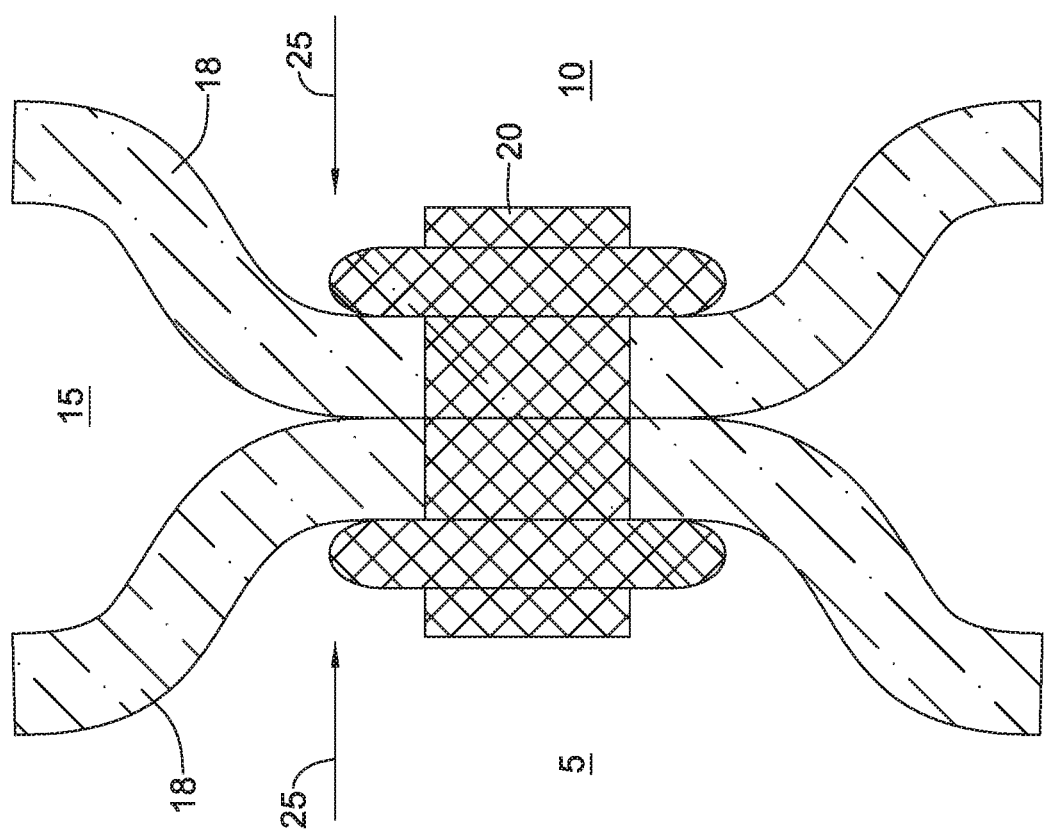
FIG. 2 is a cross-sectional view of a prior art stent disposed across vessel walls of the body vessels of FIG. 1.

Lumen apposing metal stents (LAMS) may be used for creating and maintaining an alternative path of flow through between to body lumens, for example, a gastro-jejunum or similar anastomosis that bypasses the proximal gut. This may provide an effective alternative to enteral stenting in the treatment of Gastric Outlet Obstruction (GOO). LAMS are designed to cross vessel(s) wall(s) and act as a conduit between the two body lumen structures. Conventional LAMS are generally short (e.g. 10 mm) and fairly immobile, which may lead to gastric mucosal overgrowth and 'buried stent syndrome', where the stent becomes deeply embedded in the gastric wall layers with mucosal overgrowth. Removal of the buried stent may be technically challenging. Motility in the gastric antrum may result in more vigorous traction on the stent, producing a hypertrophic response on the gastric side. When a gastro-jejunum or gastro-duodenum bypass is attempted with a conventional LAMS, similar motility of the source and target vessels may be expected to lead to this buried stent syndrome. Additionally, the independent vessels 5, 10 may be naturally spatially separated by a defined inter-vessel cavity 15, with influence from surrounding structures (e.g. Greater Omentum, Ligament of Treitz etc.), as shown in FIG. 1. Using a conventional LAMS 20 to provide a conduit between adjacent and spaced-apart vessels 5, 10, as shown in FIG. 2, reduces the inter-vessel cavity 15 and applies force, indicated by arrows 25, on the inner surface of the vessel walls 18, pressing the vessel walls 18 into contact, which may cause stress to the vessels as the vessels attempt to return to their normal spaced-apart configuration.

Figure 3:
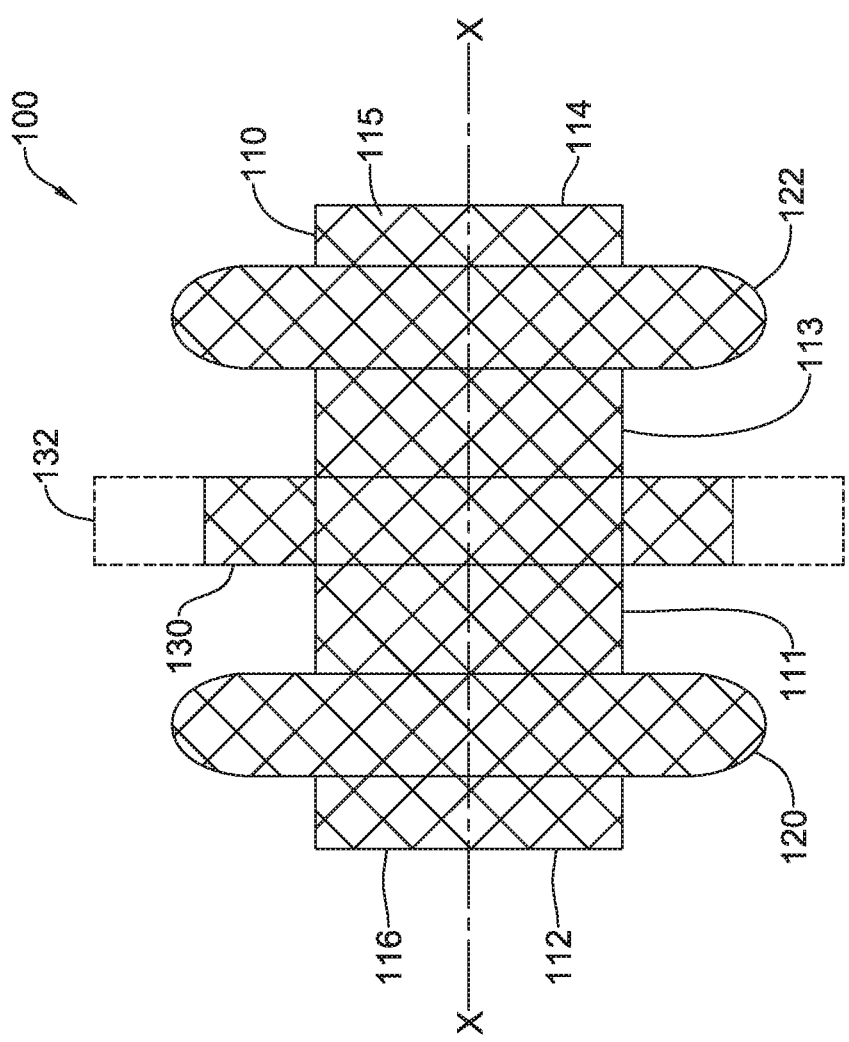
FIG. 3 is a cross-sectional view of a tubular stent in accordance with an embodiment of the disclosure.

FIG. 3 illustrates an example stent 100 that is less impactful on the surrounding anatomy while providing effective drainage between adjacent but spaced apart vessels. The stent 100 has a tubular body 110 with a first open end 112 and a second open end 114 opposite the first open end 112, and a lumen extending therethrough. The tubular body 110 may be formed from a plurality of wires 115 that may be woven, braided, wound, knitted, and combinations thereof, to form the tubular body 110. The stent 100 may include multiple wires 115 of a metal material, such as nitinol or nitinol-containing material, or other nickel-titanium alloy, for example. In some instances, the wires 115 may have a diameter of about 0.011 inches, for example. The number of wires 115 and the diameters of the wires 115, which may be the same or different, depicted in FIG. 3 are not limiting, and other numbers of wires 115 and other wire diameters may suitably be used. Desirably, an even number of wires 115 may be used, for example, from about 10 to about 36 wires 115.

Desirably, the wires 115 are made from any suitable implantable material, including without limitation nitinol, stainless steel, cobalt-based alloy such as Elgiloy®, platinum, gold, titanium, tantalum, niobium, polymeric materials and combinations thereof. Useful and nonlimiting examples of polymeric stent materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly (phosphate ester) and the like. Wires made from polymeric materials may also include radiopaque materials, such as metallic-based powders, particulates or pastes which may be incorporated into the polymeric material. For example the radiopaque material may be blended with the polymer composition from which the polymeric wire is formed, and subsequently fashioned into the stent 100 as described herein. Alternatively, the radiopaque material may be applied to the surface of the metal or polymer wire 115 of the stent 100. In either embodiment, various radiopaque materials and their salts and derivatives may be used including, without limitation, bismuth, barium and its salts such as barium sulphate, tantalum, tungsten, gold, platinum and titanium, to name a few. Additional useful radiopaque materials may be found in U.S. Pat. No. 6,626,936, the contents of which are incorporated herein by reference. Metallic complexes useful as radiopaque materials are also contemplated. The stent may be selectively made radiopaque at desired areas along the wire or may be fully radiopaque.

In some instances, the wires 115 may have a composite construction having an inner core of tantalum, gold, platinum, tungsten, iridium or combination thereof and an outer member or layer of nitinol to provide a composite wire for improved radiopacity or visibility. In one example, the inner core may be platinum and the outer layer may be nitinol. The inner core of platinum may represent about at least 10% of the wire 115 based on the overall cross-sectional percentage. Moreover, nitinol that has not been treated for shape memory such as by heating, shaping and cooling the nitinol at its martensitic and austenitic phases, is also useful as the outer layer. Further details of such composite wires may be found in U.S. Pat. No. 7,101,392, the contents of which is incorporated herein by reference. The wires 115 may be made from nitinol, or a composite wire having a central core of platinum and an outer layer of nitinol. Further, the filling weld material, if required by welding processes such as MIG, may also be made from nitinol, stainless steel, cobalt-based alloy such as Elgiloy, platinum, gold, titanium, tantalum, niobium, and combinations thereof.

The tubular body 110 defines a lumen 116 extending longitudinally between the first and second open ends 112, 114. The stent 100 may have a first anchor member 120 disposed adjacent the first open end 112 and a second anchor member 122 adjacent the second open end 114. Each of the first and second anchor members 120, 122 may extend outward from the tubular body 110, forming flanges. In the example shown in FIG. 3, the first and second anchor members 120, 122 extend circumferentially and radially outward from the tubular body 110, substantially perpendicular to the longitudinal axis x-x of the stent 100. The first and second anchor members 120, 122 may have an outer diameter larger than the outer diameter of the tubular body 110 disposed between the first and second anchor members 120, 122. The anchor members 120, 122 may be formed of portions of the wires 115 forming the tubular body 110.

The stent 100 may also include at least one divider 130 disposed between the first and second anchor members 120, 122. The divider 130 may extend outward from the tubular body 110, forming another flange intermediate the first anchor member 120 and the second anchor member 122. In the example shown in FIG. 3, the divider 130 extends circumferentially and radially outward from the tubular body 110, substantially perpendicular to the longitudinal axis of the stent 100. The divider 130 may have an outer diameter larger than the outer diameter of the tubular body 110 extending therefrom. In some examples, the divider 130 may have an outer diameter substantially the same as the outer diameters of the first and second anchor members 120, 122. In other examples, the divider 130 may have an outer diameter larger than the outer diameters of the first and second anchor members 120, 122, as indicated by dashed line 132. The divider 130 may be centrally located between the first and second open ends 112, 114 and may divide the tubular body 110 into a first saddle region 111 having a first length extending between the first anchor member 120 and the divider 130 and a second saddle region 113 having a second length extending between the second anchor member 122 and the divider 130.

The first and second anchor members 120, 122 and/or the divider 130 may be formed of portions of the wires 115 forming the tubular body 110 that extend radially outward. For example, the stent 100 may be braided, knit or woven with a plurality of wires 115 such that the tubular body 110, first and second anchor members 120, 122, and divider 130 are all braided, knit or woven from the same wires, forming a single piece, monolithic structure. The tubular body 110 may be formed to have a different flexibility than the first and second anchor members 120, 122 and/or the divider 130. For example, the first and second anchor members 120, 122 and/or the divider 130 may be less flexible than the tubular body 110. In other examples, the first and second anchor members 120, 122 and/or the divider 130 may be formed separately and then attached to the tubular body 110. For example, the first and second anchor members 120, 122 and/or the divider 130 may be formed from separate wires added to a previously formed tubular body 110.

Figure 4:
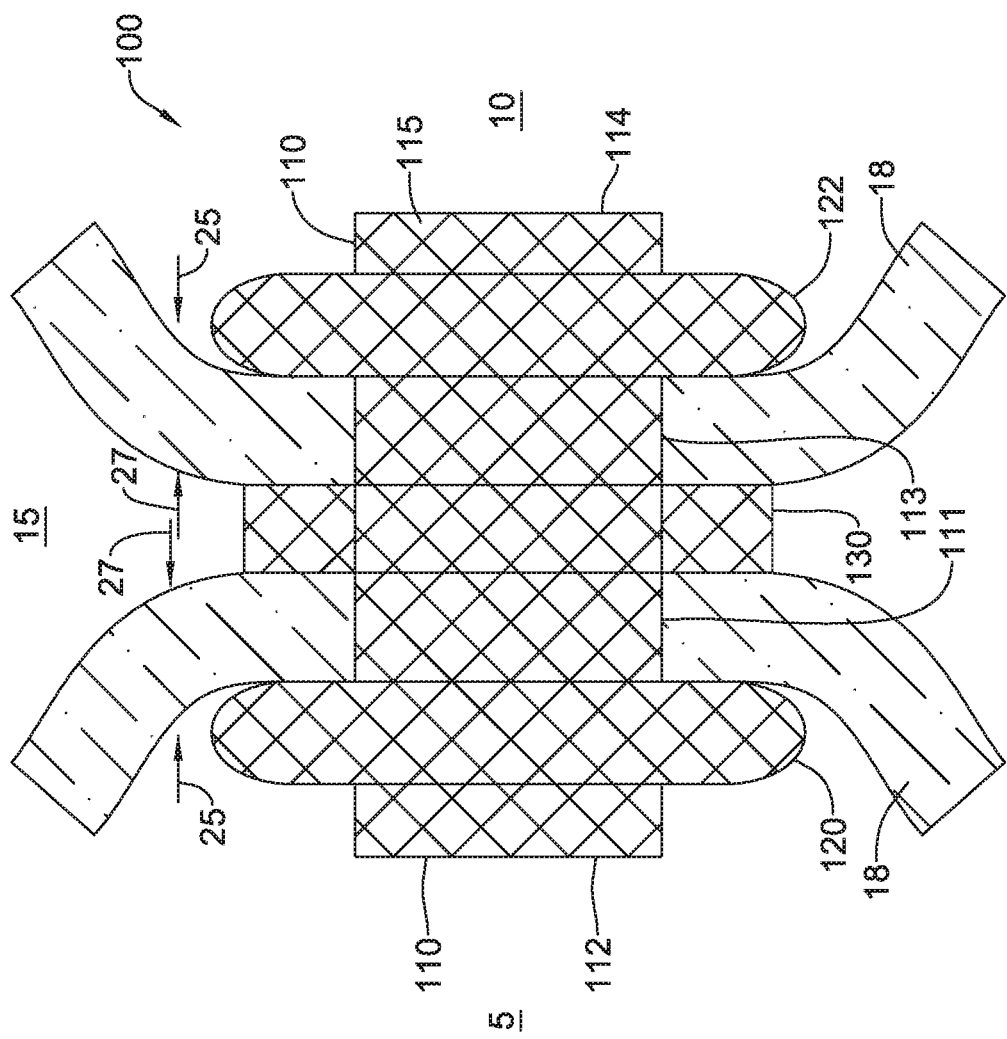
FIG. 4 is a cross-sectional view of the stent of FIG. 3 disposed across vessel walls of adjacent spaced-apart body vessels.

As shown in FIG. 4, the lengths of the first and second saddle regions 111, 113 may be sized to accommodate the vessel walls 18 of the adjacent vessels 5, 10. The divider 130 separates the vessel walls 18 and helps maintain the inter-vessel cavity 15 between the vessel walls 18. The first and second anchor members 120, 122 and the divider 130 may further hold the tubular body 110 in place relative to the vessels 5, 10, thereby forming a drainage channel between the vessels 5, 10 while acting as a spacer element to hold the vessel walls 18 in their original spaced-apart configuration. Maintaining the inter-vessel cavity 15 and keeping the vessel walls 18 in their original spaced-apart configuration may prevent gastric mucosal overgrowth and buried stent syndrome. The first and second anchor members 120, 122 and the divider 130 may also prevent the stent 100 from migrating. Further, if any force, indicated by arrows 25, is applied to the inner surface of the vessel walls 18, it is minimal, and the divider 130 applies only minimal force, indicated by arrows 27, on the outer surface of the vessel walls 18.

Figure 5:
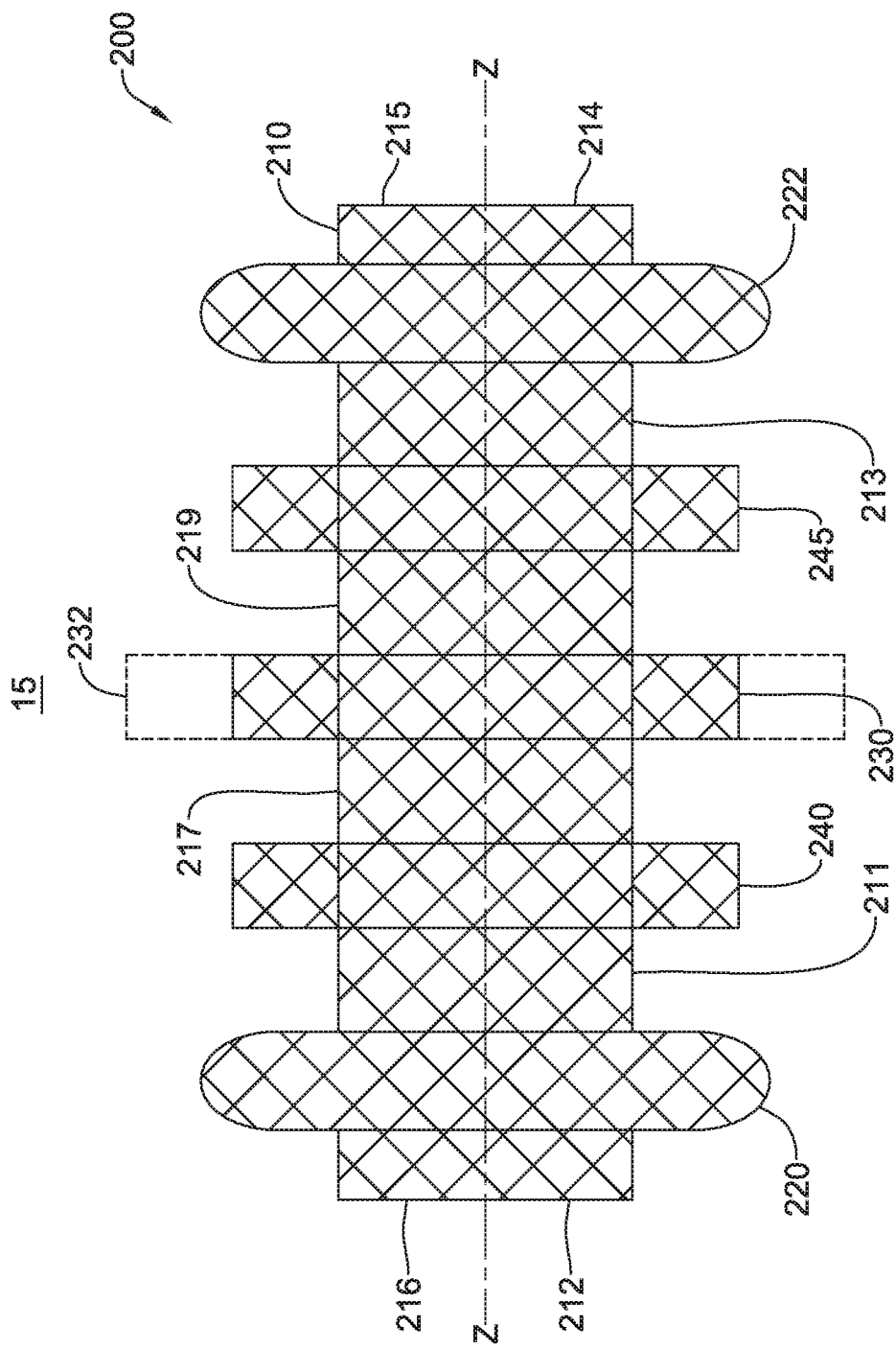
FIG. 5 is a cross-sectional view a tubular stent in accordance with another embodiment of the disclosure.

FIG. 5 illustrates another example stent 200. Similar to the stent 100 shown in FIGS. 3 and 4, the stent 200 includes a tubular body 210 defining a lumen 216 extending longitudinally between first and second open ends 212, 214, respectively. The stent 200 may have a first anchor member 220 disposed adjacent the first open end 212 and a second anchor member 222 adjacent the second open end 214. Each of the first and second anchor members 220, 222 may extend outward from the tubular body 210, forming flanges. In the example shown in FIG. 5, the first and second anchor members 220, 222 extend circumferentially and radially outward from the tubular body 210, substantially perpendicular to the longitudinal axis z-z of the stent 200. The first and second anchor members 220, 222 may have an outer diameter larger than the outer diameter of the tubular body 210 disposed between the first and second anchor members 220, 222. The stent 200 may also include a center divider 230 disposed centrally between the first and second anchor members 220, 222.

Stent 200 differs from stent 100 in that stent 200 may include a first side divider 240 disposed between the first anchor member 220 and the center divider 230, and second side divider 245 disposed between the second anchor member 222 and the center divider 230. The center divider 230 and first and second side dividers 240, 245 may extend outward from the tubular body 210, forming additional flanges. In the example shown in FIG. 5, the center divider 230 and first and second side dividers 240, 245 extend circumferentially and radially outward from the tubular body 210, substantially perpendicular to the longitudinal axis of the stent 200. The center divider 230 and first and second side dividers 240, 245 may all have an outer diameter larger than the outer diameter of the tubular body 210 extending therebetween. In some examples, the center divider 230 and first and second side dividers 240, 245 may have an outer diameter substantially the same as the outer diameters of the first and second anchor members 220, 222. In other examples, the center divider 230 may have an outer diameter greater than the outer diameters of the first and second anchor members 220, 222 and the first and second side dividers 240, 245, as indicated by dashed line 232. The center divider 230, first and second side dividers 240, 245, and the first and second anchor members 220, 222 may all have the same flexibility, which may be the same as the tubular body 210. In other examples, the center divider 230 may be less flexible than the first and second side dividers 240, 245 and/or the first and second anchor members 220, 222.

Figure 6:
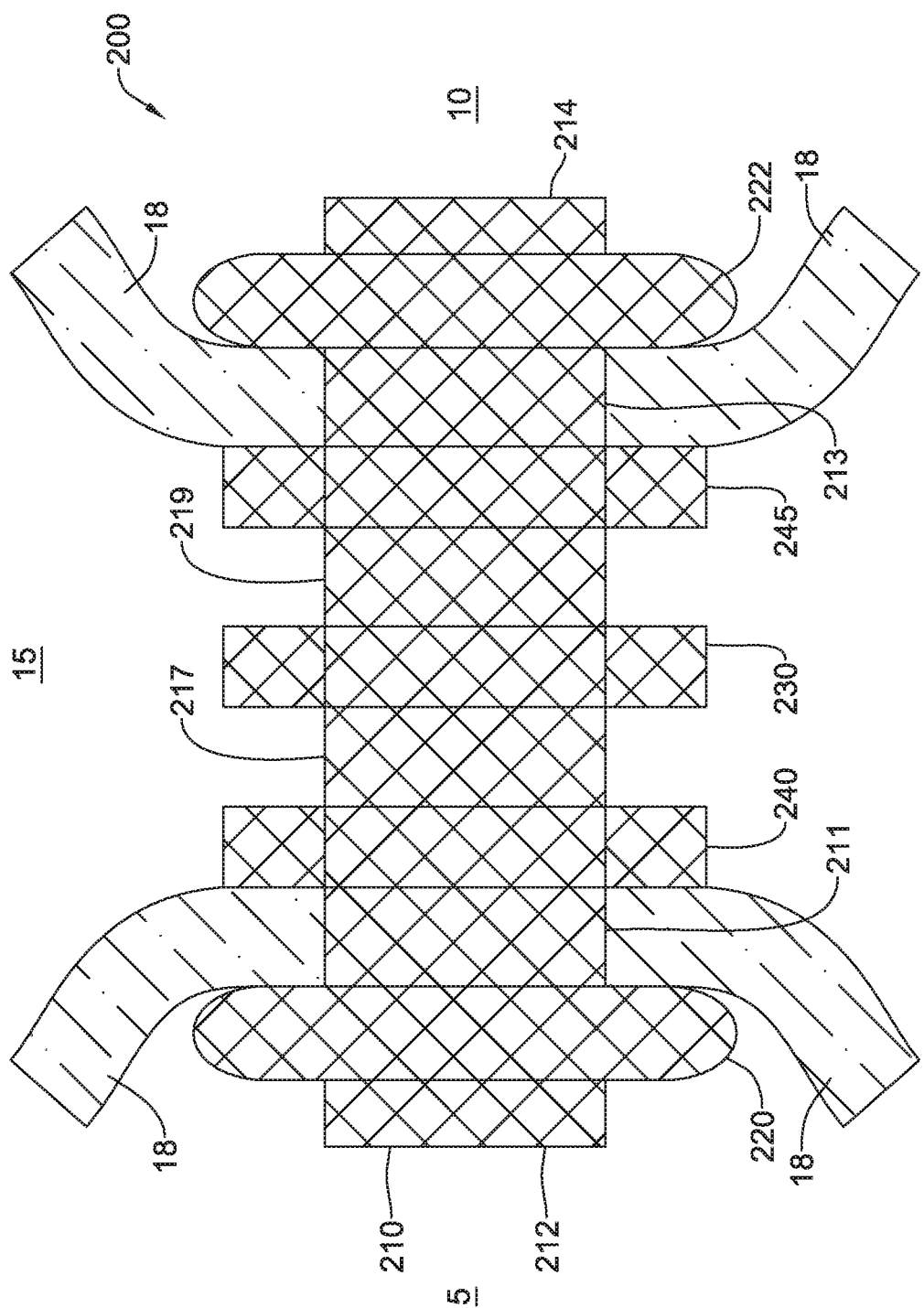
FIG. 6 is a cross-sectional view of the stent of FIG. 5 disposed across vessel walls of adjacent spaced-apart body vessels.

Stent 200 may capture each of the two spaced-apart vessel walls 18 within their own bi-flanged region. For example, the center divider 230 and first and second side dividers 240, 245 may divide the tubular body 210 into a first saddle region 211 having a first length extending between the first anchor member 220 and the first side divider 240, a second saddle region 213 having a second length extending between the second anchor member 222 and the second side divider 245, a third saddle region 217 having a third length extending between the first side divider 240 and the center divider 230, and a fourth saddle region 219 having a fourth length extending between the center divider 230 and the second side divider 245. As shown in FIG. 6, the vessel walls 18 are held in separate, spaced-apart first and second saddle regions 211, 213. The center divider 230 and the third and fourth saddle regions 217, 219 act as a spacer component, keeping the vessel walls 18 spaced apart to maintain the anatomy in a configuration the same as or similar to the natural configuration.

As with the stent 100, any of the first and second anchor members 220, 222, the center divider 230, and the first and second side dividers 240, 245 may be portions of the tubular body 210 that extend radially outward. For example, the stent 200 may be braided, knit or woven with a plurality of wires 215 such that the tubular body 210, first and second anchor members 220, 222, the center divider 230, and the first and second side dividers 240, 245 are all a single piece, monolithic structure. The tubular body 210 may be formed to have a different flexibility than the first and second anchor members 220, 222, the center divider 230, and the first and second side dividers 240, 245. For example, one or more of the first and second anchor members 220, 222, the center divider 230, and the first and second side dividers 240, 245 may be stiffer than the tubular body 210. In other examples, any of the first and second anchor members 220, 222, the center divider 230, and the first and second side dividers 240, 245 may be formed separately and then attached to the tubular body 210. For example, the first and second anchor members 120, 122, the center divider 230, and the first and second side dividers 240, 245 may be formed from additional wires added to a previously formed tubular body 210.

As shown in FIG. 6, the lengths of the first and second saddle regions 211, 213 may be sized to accommodate the vessel walls 18 of the adjacent vessels 5, 10. The first and second side dividers 240, 245 separate the vessel walls 18 and help maintain the inter-vessel cavity 15. The first and second anchor members 220, 222 and the first and second side dividers 240, 245 may further hold the tubular body 210 in place relative to the vessels 5, 10, thereby forming a drainage channel between the vessels 5, 10 while acting as a spacer element to hold the vessel walls 18 in a spaced-apart configuration similar to their original configuration. The first and second anchor members 220, 222 and the first and second side dividers 240, 245 may also prevent the stent 200 from migrating.

Figure 7A:
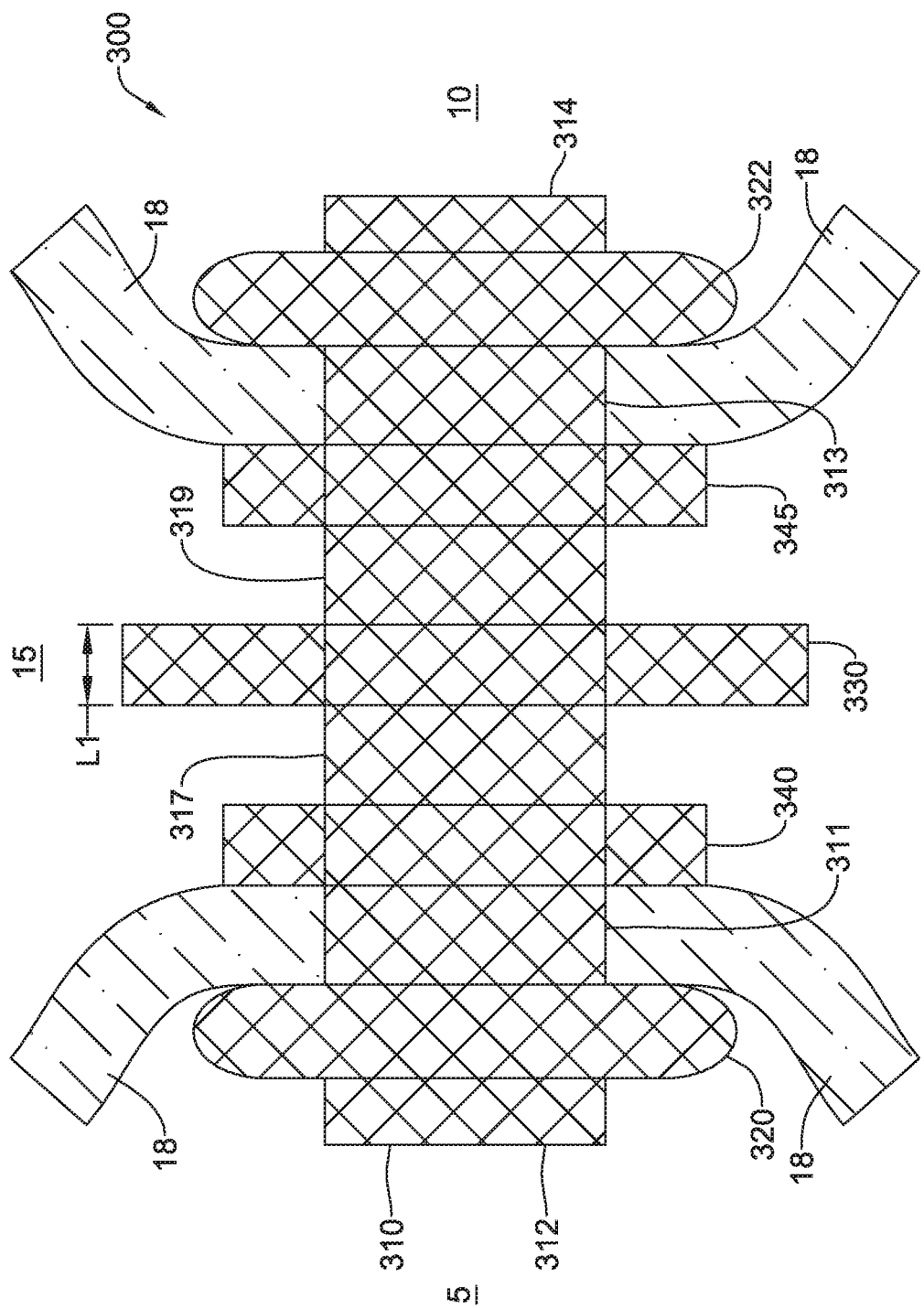
FIG. 7A is a cross-sectional view of a tubular stent in a first configuration in accordance with another embodiment of the disclosure, disposed across vessel walls of adjacent spaced-apart body vessels.

FIGS. 7A and 7B illustrate another embodiment of stent 300 that includes an expandable center divider 330. This stent 300 may be used in locations where the inter-vessel cavity 15 between vessels 5, 10 is relatively small, as shown in FIG. 7A, by positioning the center divider 330 in a first, axially contracted configuration. The same stent 300 may also be used in locations where the inter-vessel cavity 17 is much larger, as shown in FIG. 7B, by moving the center divider 330 into a second, axially expanded configuration. The expandable center divider 330 allows the same stent 300 to be used in either location, giving the stent 300 a wider range of use.

Stent 300 may have a tubular body 310, first and second anchor members 320, 322, and first and second side dividers 340, 345 identical to the tubular body 210, first and second anchor members 220, 222, and first and second side dividers 240, 245 described above with reference to stent 200. As described above with reference to stent 200, the first and second anchor members 320, 322, center divider 330, and first and second side dividers 340, 345 may divide the tubular body 310 of stent 300 into a first saddle region 311 having a first length extending between the first anchor member 320 and the first side divider 340, a second saddle region 313 having a second length extending between the second anchor member 322 and the second side divider 345, a third saddle region 317 having a third length extending between the first side divider 340 and the center divider 330, and a fourth saddle region 319 having a fourth length extending between the center divider 330 and the second side divider 345.

Stent 300 differs from stent 200 in that the center divider 330 is axially expandable and/or axially contractible. In the embodiment shown in FIG. 7A, the center divider 330 has a first, axially contracted configuration in which the center divider 330 has a first axial length L1 and an outer diameter larger than the outer diameters of the first and second anchor members 320, 322 and the first and second side dividers 340, 345. The center divider 330 may be expanded to a second, axially expanded configuration in which the center divider 330 has a second axial length L2 that is greater than the first axial length L1, as shown in FIG. 7B. As shown in FIG. 7B, in the second, axially expanded configuration, the center divider 330 has compressed radially such that it has an outer diameter substantially the same as the outer diameter of the tubular body 310. The center divider 330 may also have an infinite number of intermediate positions between the first, axially contracted configuration shown in FIG. 7A, and the second, axially expanded configuration shown in FIG. 7B. These intermediate positions may be achieved by expanding or contracting the center divider 330 to have any length between L1 and L2. Expanding the center divider 330 results in an increase in the length of the third and fourth saddle regions 317, 319, resulting in an increase in the longitudinal length of the stent 300. As seen in FIG. 7B, when the center divider 330 is in the fully expanded configuration, the third and fourth saddle regions 317, 319 merge, forming a single combined middle saddle region 316. The first and second anchor members 320, 322 and the first and second side dividers 340, 345 do not move relative to one another, thus the first and second saddle regions 311, 313 have a constant size to retain the vessel walls 18, 28, regardless of whether the center divider 330 is in the axially contracted configuration, as shown in FIG. 7A, or in the axially expanded configuration, as shown in FIG. 7B.

The ability of the stent 300 to have a variety of overall lengths and distances between the first and second saddle regions 311, 313 holding the vessel walls 18, 28, provides the advantage of using a single stent 300 in a wide variety of body locations, with varying inter-vessel cavity sizes and distances between adjacent vessel walls 18, 28.

The center divider 330 may be formed in a manner that allows for it to be contractible and expandable, axially contracting into the configuration shown in FIG. 7A when the natural vessel spacing is relatively small and axially expanding and flattening out into a low profile configuration shown in FIG. 7B when the natural vessel spacing is greater. The stent 300 may be braided from a plurality of wires, with the longitudinal and/or radial braiding angle of the center divider 330 selected to allow the center divider 330 to be moved between the first, axially contracted configuration of FIG. 7A, through infinite intermediate configurations, to the second, axially expanded configuration of FIG. 7B, and to stay in any axial position. The stent 300 may be manually moved between the first and second axial configurations by grasping the first and second anchor members 320, 322 and pulling them apart or pushing them together.

FIG. 8 illustrates an alternative embodiment of a stent 400 with a coating 450 covering the outer surface of the stent, including the tubular body 410, first and second anchor members 420, 422, center divider 430, and first and second side dividers 440, 445 if present. The coating 450 may fully cover the entire length of the stent 400, forming a fully covered stent in which all of the interstices defined in the braided or woven pattern are covered with the coating 450, thereby preventing tissue in-growth and fluid leakage into the inter-vessel cavity 15. In other examples, the coating 450 may cover only a portion of the length of the stent 400, forming a partially covered stent in which a portion of the interstices defined in the braided or woven pattern remain uncovered, allowing tissue in-growth. For example, the coating 450 may be disposed only over the middle portion of the stent that will be disposed in the inter-vessel cavity 15, including the first and second side dividers 440, 445, the third and fourth saddle regions 417, 419, and the center divider 430.

The coating 450 may be formed with a sleeve portion 452 that initially extends beyond the first open end 412 of the stent 400, but is then turned inside out, as indicated by arrows 460, and inserted within the lumen 416. The sleeve portion 452 may be freely floating within the lumen 416, and not attached at any point to the inner surface of the tubular body 410. For example, the base end of the sleeve portion 452 may be secured to the tubular framework of the stent 410 at the first end 412, with the sleeve portion 452 extending through the lumen 416 toward the second end 414, to the second end 414 and/or beyond the second end 414 to a free end 454 of the sleeve portion 452. In some instances, the free end 454 may extend beyond the second open end 414 of the stent 400, as shown in FIG. 8. The sleeve portion 452 may not be attached to the tubular framework of the stent 400 at any locations other than the base end of the sleeve portion 452 at the first end 412. It will be understood that the coating 450 may be disposed on the stents 100, 200, 300 as well, in the manner described above. The sleeve portion 452 may define a lumen extending therethrough, and the sleeve portion 452, such as the free end 454 of the sleeve portion 452, or another portion of the sleeve portion 452, may be configured to collapse upon itself to close off the lumen through the sleeve portion 452.

In some examples, the stent 400 may be dipped into a solution of silicone or other polymer to form the coating 450. In other examples, a polymer sheet or tube may be placed around or within the stent 400 to form the coating 450. The coating 450 may be disposed on external or internal surfaces of the stent 400, or on both the internal and external surfaces of the stent 400, thereby embedding the stent 400 in the polymeric material. The coating 450 may be a polymer covering, such as a polytetrafluoroethylene (PTFE) or silicone covering, however other coverings, particularly elastomeric polymers, may be used. Non-limiting examples of useful polymeric materials include polyesters, polypropylenes, polyethylenes, polyurethanes, polynaphthalenes, polytetrafluoroethylenes, expanded polytetrafluoroethylene, silicone, and combinations and copolymers thereof.

The coating 450 may be formed by using an elongated coating mandrel that is shaped to fit the stent 400, and continues in a direction beyond the first open end 412 for a length that matches the desired length of the sleeve portion 452. The coating 450 is then applied to the stent 400 and the coating mandrel, such as by spray coating. Once the coating 450 has dried or cured, the sleeve portion 452 may be tucked back through the lumen 416 of the stent 400 such that the sleeve portion 452 freely floats within the stent 400 and the free end 454 protrudes beyond the second open end 414 of the stent 400, as shown in FIG. 8. In other examples, the coating 450 may be disposed over the inner surface of the stent 400 between the first and second open ends 412, 414, with the sleeve portion 452 extending from the first open end 412 and then turned back into the lumen 416.

The coating 450 may be expandable and contractible with any expansion and contraction of the stent 400. The coating 450 on the outer surface of the stent may aid in gripping the vessel walls 18 and may protect the vessel walls 18 from any damage that may result from wires forming the stent impinging on the vessel walls 18. In some examples, the coating 450 may be silicone.

When a LAMS device is disposed within the digestive tract, the digestive cycle can cause unwanted flow of substances in a reverse direction into organs that initially required drainage. The sleeve portion 452 of the coating 450 may function as a one-way valve. The sleeve portion 452 within the stent lumen 416 may be primarily in a collapsed or closed off state due to the non-supported nature of the sleeve portion 452 and the weight of the coating material. Drainage from the area of interest, such as vessel 5, will be able to push through the sleeve portion 452 from the supported open end at the first open end 412 of the stent, and out the free end 454 into the vessel 10, as indicated by dashed arrow 470, but reverse flow from vessel 10 into vessel 5 will be difficult if not impossible due to the collapsing nature of the sleeve portion 452 and particularly the free end 454. The length of the sleeve portion 452 may be formed longer or shorter depending on the location where effective drainage is to be routed. The stent 400 with coating 450 may be used in specific clinical scenarios where drainage from a region is required but bypassing of adjacent vessels, fistulae or treatment locations may be advantageous. A longer sleeve portion 452 will allow for drainage to begin at the drainage site but allow the fluid to be routed past a less desirable location to a more neutral drainage destination.

In some embodiments, the sleeve portion 452 may have a tapered configuration, extending from the portion attached to the outer surface of the stent at the first open end 412 and narrowing to the free end 454, as indicated by dashed line 453. Such a tapered sleeve portion 453 may provide increased closure of the sleeve portion. A more tapered free end 454 may provide a narrower exit, potentially more suited to less viscous fluid flow, whereas a wider free end 454 may be potentially more suited to drainage of suspensions of higher viscosity.

The lengths of the first and second saddle regions 111, 113, 211, 213, 311, 313, 411, 413 may be selected to receive a particular vessel wall 18, 28. In some examples, these first and second saddle regions may be between 5 mm and 20 mm. In other examples, these first and second saddle regions may be between 10 mm and 15 mm. The third and fourth saddle regions 217, 219, 317, 319, 417, 419 may have similar lengths, or may be shorter or longer, depending on the width of the inter-vessel cavity 15, 17 across which the stent 200, 300, 400 will be disposed. In the stent 300 with an expandable center divider 330, in some examples, the length of the third and fourth saddle regions 317, 319 may be between 5 mm and 15 mm when the stent 300 is in the first, axially contracted configuration, and the single combined middle saddle region 316 may have a length of between 10 mm and 30 mm when the stent is in the second, axially expanded configuration.

In some examples, the entire length of the stent 100, 200, 300, 400 may be 40 mm to 60 mm and the diameter of the tubular body 110, 210, 310, 410 may be 20 mm to 30 mm. The flange elements, including the first and second anchor members 120, 122, 220, 222, 320, 322, 420, 422, divider 130, and first and second side dividers 240, 245, 340, 345, 440, 445 may extend radially beyond the outer surface of the tubular body 110, 210, 310, 410 by between 5 mm and 20 mm. In some examples, these flange elements may extend beyond the outer surface of the tubular body 110, 210, 310, 410 by between 5 mm and 15 mm. The flange elements may extend radially beyond the outer surface to different extents at the first and second open ends 112, 114, 212, 214, 312, 314, 412, 414 of the stent. For example, the first anchor member 120, 220, 320, 420 and divider 130 or first side divider 240, 340, 440 may extend radially outward from the tubular body 110, 210, 310, 410 further than the corresponding elements at the second open end 114, 214, 314, 414. This may provide the advantage of providing stronger anti-migration features adjacent a first vessel 5, 7 that may experience more movement or apply more pressure on the stent during normal body functions than a second vessel 10, 12.

FIGS. 4, 6, 7A, 7B, and 8 show the stent 100, 200, 300, 400 implanted in a body site including a first vessel 5, 7 and a second vessel 10, 12 separated by an inter-vessel cavity 15, 17. In a method of draining fluid from the first vessel 5, 7 across the inter-vessel cavity 15, 17, and into the second vessel 10, 12, the first open end 112, 212, 312, 412 and first anchor member 120, 220, 320, 420 of the stent 100, 200, 300, 400 may be implanted through an opening in the vessel wall 18, 28 with the first anchor member 120, 220, 320, 420 contacting the interior of the vessel wall 18, 28. In the case of the stent 100, the vessel wall 18 of vessel 5 is held between the first anchor member 120 and the divider 130, and the vessel wall 18 of vessel 10 is held between the divider 130 and the second anchor member 122. In the case of stents 200, 300, 400, the vessel wall 18, 28 of vessel 5, 7 is held between the first anchor member 220, 320, 420 and the first side divider 240, 340, 440, and the vessel wall 18 of vessel 10, 12 is held between the second side divider 245, 345, 445 and the second anchor member 222, 322, 422. The vessel walls 18, 28 are thus held in their natural spaced-apart anatomical orientation. The enlarged diameters of the first and second anchor members 120, 122, 220, 222, 320, 322, 420, 422, divider 130, first and second side dividers 240, 245, 340, 345, 440, 445, anchor the stent 100, 200, 300, 400 in place and prevent migration of the stent Various stent types and stent constructions may be employed for the stent 100, 200, 300, 400. For example, the stent 100, 200, 300, 400 may be a self-expanding stent or a balloon expandable stent. The stent 100, 200, 300, 400 may be capable of radially contracting to a compressed or collapsed configuration for delivery, and then expandable to an expanded configuration during deployment in the body vessels. Thus, the stent 100, 200, 300, 400 may be described as radially distensible or deformable. Self-expanding stents include those that have a spring-like action which causes the stent to radially expand, or stents which expand due to the memory properties of the stent material for a particular configuration at a certain temperature. The configuration of the stent may also be chosen from a host of geometries. For example, wire stents can be fastened into a continuous helical pattern, with or without a wave-like or zig-zag in the wire, to form a radially deformable stent. Individual rings or circular members can be linked together such as by struts, sutures, welding or interlacing or locking of the rings to form a tubular stent. In other embodiments, the stent 100, 200, 300, 400 may be formed as a monolithic tubular member by etching or cutting a pattern of interconnected struts from a tube.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A stent comprising:
    a tubular body formed of one or more interwoven wires, the tubular body having first and second opposing open ends and a lumen extending therebetween, the tubular body defining a longitudinal axis and a length extending between the first and second open ends;
    a first anchor member disposed adjacent the first open end and a second anchor member disposed adjacent the second open end, the first and second anchor members each extending radially outward from the tubular body, the first and second anchor members each having an outer diameter larger than an outer diameter of the tubular body disposed between the first and second anchor members; and
    a first side divider, a second side divider, and a central divider disposed between the first and second anchor members, the first side divider, the second side divider, and the central divider extending radially outward from the tubular body and each having an outer diameter larger than the outer diameter of the tubular body, the first side divider, the second side divider, and the central divider dividing the tubular body into at least a first saddle region extending between the first anchor member and the first side divider, a second saddle region extending between the second anchor member and the second side divider, a third saddle region extending between the first side divider and the central divider, and a fourth saddle region extending between the second side divider and the central divider;
    wherein the central divider is moveable between a first, contracted configuration in which the central divider has a first axial length, and a second, expanded configuration in which the central divider has a second axial length greater than the first axial length, the central divider expanding axially while compressing radially as it moves from the first configuration to the second configuration such that when in the second configuration the central divider has an outer diameter substantially the same as an outer diameter of the tubular body between the first and second anchor members;
    wherein the tubular body is configured such that moving the central divider between the first and second configurations maintains a constant axial length of the first and second saddle regions.

2. The stent of claim 1, wherein the first and second anchor members are interwoven with the tubular body and wherein the outer diameter of the first and second anchor members remains constant as the central divider moves between the first and second configurations.

3. The stent of claim 1, wherein the first and second anchor members are less flexible than the tubular body.

4. The stent of claim 1, wherein the at least one divider has an outer diameter larger than outer diameters of the first and second anchor members.

5. The stent of claim 1, wherein the central divider has an outer diameter greater than outer diameters of the first and second side dividers.

6. The stent of claim 1, wherein the central divider is more flexible than the first and second side dividers.

7. The stent of claim 1, wherein the length of the tubular body increases as the central divider moves between the first and second configurations.

8. The stent of claim 7, wherein the outer diameter of the tubular body remains constant as the central divider moves between the first and second configurations.

9. The stent of claim 7, wherein the central divider is configured to remain in the first configuration when manually moved into the first configuration, and to remain in the second configuration when manually moved into the second configuration.

10. The stent of claim 1, further comprising a covering extending over an entirety of an outer surface of the tubular body, first and second anchor members, and the at least one divider.

11. The stent of claim 10, wherein the covering extends longitudinally beyond the first end of the tubular body, forming a collapsible tubular sleeve, wherein the collapsible tubular sleeve is configured to be inverted and to extend through the lumen of the tubular body from the first end of the tubular body to a free end of the collapsible tubular sleeve extending beyond the second end of the tubular body.

12. The stent of claim 11, wherein the collapsible tubular sleeve defines a one-way valve, only allowing fluid to pass from the first end of the tubular body, through the collapsible tubular sleeve, and out the free end of the collapsible tubular sleeve.

13. The stent of claim 1, wherein the first and second anchor members and the at least one divider extend perpendicular to the longitudinal axis.

14. A stent comprising:
a tubular body formed of one or more interwoven wires, the tubular body having first and second opposing open ends and a lumen extending therebetween, the tubular body defining a longitudinal axis and a length extending between the first and second open ends; and
a plurality of longitudinally spaced apart anchor members extending radially outward from the tubular body, the anchor members each having an outer diameter larger than an outer diameter of the tubular body disposed between the anchor members, the plurality of anchor members dividing the tubular body into at least a first saddle region extending between a first anchor member adjacent the first end and a first side anchor member, a second saddle region extending between a second anchor member adjacent the second end and a second side anchor member, a third saddle region extending between the first side anchor member and a center anchor member, and a fourth saddle region extending between the second side anchor member and the center anchor member;
wherein the center anchor member is moveable between a first, contracted configuration in which the center anchor member has a first axial length, and a second, expanded configuration in which the center anchor member has a second axial length greater than the first axial length, the center anchor member expanding axially while compressing radially as it moves from the first configuration to the second configuration such that when in the second configuration the outer diameter of the center anchor member is substantially the same as the outer diameter of the tubular body;
wherein the tubular body is configured such that moving the center divider between the first and second configurations maintains a constant axial length of the first and second saddle regions.

15. The stent of claim 14, wherein the length of the tubular body increases and the outer diameter of the tubular body remains constant as the center anchor member moves between the first and second configurations.

16. The stent of claim 15, wherein the center anchor member is configured to remain in the first configuration when manually moved into the first configuration, and to remain in the second configuration when manually moved into the second configuration.

17. The stent of claim 14, further comprising a covering extending over an entirety of an outer surface of the tubular body and the first, second, and center anchor members, wherein the covering extends longitudinally beyond the first end of the tubular body, forming a collapsible tubular sleeve, wherein the collapsible tubular sleeve is configured to be inverted and to extend through the lumen of the tubular body from the first end of the tubular body to a free end extending beyond the second end of the tubular body.

18. The stent of claim 14, wherein the outer diameter of the first and second anchor members remains constant as the center anchor member moves between the first and second configurations.

* * * * *